(12) United States Patent
Tsuji et al.

(10) Patent No.: US 7,723,025 B2
(45) Date of Patent: May 25, 2010

(54) METHOD FOR EVALUATING QUALITY OF BEEF SUCH AS TASTE AND TEXTURE ON THE BASIS OF GENOTYPE OF STEAROYL-COA DESATURASE

(75) Inventors: Soichi Tsuji, Kawanishi (JP); Hideyuki Mannen, Kobe (JP); Masaaki Taniguchi, Kobe (JP)

(73) Assignee: The New Industry Research Organization, Hyogo (JP)

( * ) Notice: Subject to any disclaimer, the term of this patent is extended or adjusted under 35 U.S.C. 154(b) by 1033 days.

(21) Appl. No.: 10/545,611

(22) PCT Filed: Feb. 17, 2004

(86) PCT No.: PCT/JP2004/001756
§ 371 (c)(1),
(2), (4) Date: Aug. 16, 2005

(87) PCT Pub. No.: WO2004/074515
PCT Pub. Date: Sep. 2, 2004

(65) Prior Publication Data
US 2007/0077558 A1      Apr. 5, 2007

(30) Foreign Application Priority Data
Feb. 20, 2003    (JP) ............................. 2003-042076

(51) Int. Cl.
*C12Q 1/68*       (2006.01)
*C12P 19/34*     (2006.01)
(52) U.S. Cl. ......................................... 435/6; 435/91.2
(58) Field of Classification Search ...................... None
See application file for complete search history.

(56) References Cited

FOREIGN PATENT DOCUMENTS

WO        WO 03/007705 A1      1/2003

OTHER PUBLICATIONS

GenBank Locus AB075020 'Bos taurus Scd mRNA for stearoyl-CoA desaturase, complete cds.' Jan 8, 2003, GI:27544003, from www.ncbi.nlm.nih.gov, pp. 1-4.*
Chung M. et al 'Cloning and characterization of bovine stearoyl CoA desaturase1 cDNA from adipose tissues' Biosci. Biotechnol. Biochem. (2000) 64 (7), 1526-1530.*
Taniguchi M. et al 'Genotype of stearoyl-coA desaturase is associated with fatty acid composition in Japanese Black cattle.' Mamm Genome. Feb. 2004;15(2):142-8. Includes Dated Table of Contents.*
Moioli B et al 'Short communication: Effect of stearoyl-coenzyme A desaturase polymorphism on fatty acid composition of milk.' J Dairy Sci. Jul. 2007;90(7):3553-8.*
Hacker U.T. et al, Gut (May 1997), p. 623-627.*
International Search Report from Patent Cooperation Treaty issued on Jun. 22, 2004 for the corresponding PCT patent application No. PCT/JP2004/001756.
Written Opinion from Patent Cooperation Treaty issued on Jun. 22, 2004 for the corresponding PCT patent application No. PCT/JP2004/001756.
Zembayashi, Meiji et al., "Reducing Saturated Fatty Acid Content in Beef by Genetic Selection." *The Ito Foundation* vol. 12 (1994): pp. 214-219.
Wilson, J.J. et al., "Rapid Communication: a TaqI Restriction Fragment Length Polymorphism in the Stearoyl-CoA Desaturase Gene in DNA from Purebred Japanese Black Cattle." J. Anim. Sci. vol. 71, No. 9 (1993): p. 2575.
Medrano, J.F. et al., "Genetic Modification of the Composition of Milk Fat: Identification of Polymorphisms Within the Bovine Stearoyl-CoA-Desaturase Gene." Pfluergers Arch. Eur. J. Physiol. vol. 439, No. 3 (2000): Supp. p. R 24.
Chung, M. et al., "Cloning and Characterization of Bovine Stearoyl CoA Desaturase1 cDNA from Adipose Tissues." Biosci. Biotechnol. Biochem. vol. 64, No. 7 (2000): pp. 1526-1530.
Cameron, P. J. et al., "Stearoyl Coenzyme A Desaturase Enzyme Activity and MRNA Levels Are Not Different in Subcutaneous Adipose Tissue from Angu and American Wagyu Steers," Journal of Animal Science, vol. 72, No. 10, (1994): pp. 2624-2628.
Supplemental European Search Report dated Jun. 12, 2006 in corresponding European Patent Application No. 04711722.1.2401.
Office Communication from European Patent Office issued on Sep. 14, 2006 for the corresponding European patent application No. 04 711 722.1.
Oka, A. et al., "Genetic Effects on Fatty Acid Composition of Carcass Fat of Japanese Black Wagyu Steers." *J. Anim. Sci.* vol. 80. No. 4. (2002): pp. 1005-1011.
Yao, J. et al., "Generation of EST and cDNA Microarray Resources for the Study of Bovine Immunobiology." *Acta Veterinaria Scandinavica*. vol. 42. No. 3. (2001): pp. 391-405.
Coussens, Paul M. et al., "Gene Expression Profiling of Peripheral Blood Mononuclear Cells from Cattle Infected with *Myobacterium Paratuberculosis*." *American Society of Microbiology*. vol. 70. No. 10. (2002): pp. 7-9.

* cited by examiner

*Primary Examiner*—Stephen Kapushoc
(74) *Attorney, Agent, or Firm*—Posz Law Group, PLC

(57) ABSTRACT

We paid attention to stearoyl-CoA desaturase gene, and investigated the relation between this gene and the unsaturated fatty acid content in beef fat. As a result, we found that the unsaturated fatty acid content was associated with the genotype of this gene, classified according to several single nucleotide polymorphisms (SNPs) on this gene. The present invention is a method to predict the unsaturated fatty acid content in beef (or milk) fat, on the basis of the genotype of bovine stearoyl-CoA desaturase, and useful prediction method for beef quality such as taste and texture.

6 Claims, 3 Drawing Sheets

FIG.2

ATGCCGGCCCACTTGCTGCAAGAGGAGATCTCTAGCTCCTACACAACCACCACCACCATCACA
GCACCTCCTTCCAGGGTCCTGCAGAATGGAGGGGGCAAATTGGAGAAGACTCCCCTATACTTG
GAAGAAGACATCCGCCCTGAAATGAGAGATGACATCTATGACCCAACTTACCAGGATAAGGAG
GGCCCAAAGCCCAAGCTTGAGTATGTTTGGAGAAACATCATCCTCATGTCTCTGTTACACTTG
GGAGCCCTATATGGGATCACATTGATCCCCACCTGCAAGATATACACCTATATCTGGGTGTTA
TTCTACTATCTGATGGGTGCCCTGGGCATCACAGCAGGGGCCCATCGCCTGTGGAGTCACCGA
ACCTACAAAGCTCGGCTGCCTCTGCGGGTCTTCCTGATCATTGGCAACACCATGGCGTTCCAG
AATGACGTTTTTGAATGGTCCCGAGATCACCGTGCCCACCACAAGTTTTCAGAAACGGATGCC
GACCCCCACAATTCCCGACGTGGCTTTTTCTTCTCACGTGGGTTGGCTGCTTGTGCGCAAA
CACCCAGCTGTCAAAGAAAAGGGTTCCACGCTAAATTTATCCGACCTAAGAGCCGAGAAGCTG
GTGATGTTCCAGAGGAGGTACTACAAACCTGGTGTCCTGTTGTTGTGCTTCATCCTGCCCACA
                                          Forward Primer →

CTCGTG[CCATGG]TATCTGTGGGATGAAACGTTTCAAAACAGCCTGTTTTTTGCCACCTTATTC
CGTTATGCCCTTGGGCTCAACGTCACCTGGCTGGTGAATAGTGCTGCCCATATGTATGGATAC
CGCCCTTATGACAAGACCATCAACCCCCGAGAGAATATTCTGGTTTCCCTGGGAGCT[GCG]GGT
         ← Reverse Primer GAGGGCTTCCACAACTACCACCACACCTTTCCTTATGACTACTCAGCCAGTGAGTACCGCTGG
CACATCAACTTTACCACGTTCTTCATTGATTGCATGGCTGCCATCGGTCTGGCTTATGACCGG
AAGAAAGTATCCAAGGCTGCCATCTTGGCCAGGATAATAAGAACTGGAGAGGAAAGCTACAAG
AGTGGCTGA

SEQUENCE LISTING

<160> NUMBER OF SEQ ID NOS: 14

<210> SEQ ID NO 1
<211> LENGTH: 4964
<212> TYPE: DNA
<213> ORGANISM: Bos taurus

<400> SEQUENCE: 1

```
atgccggccc acttgctgca agaggagatc tctagctcct acacaaccac caccaccatc      60
acagcacctc cttccagggt cctgcagaat ggaggggggca aattggagaa gactcccta     120 tacttggaag aagacatccg ccctgaaatg agagatgaca tctatgaccc aacttaccag     180
gataaggagg gcccaaagcc caagcttgag tatgtttgga gaaacatcat cctcatgtct     240
ctgttacact tgggagccct atatgggatc acattgatcc ccacctgcaa gatatacacc     300
tatatctggg tgttattcta ctatctgatg ggtgccctgg gcatcacagc aggggcccat     360
cgcctgtgga gtcaccgaac ctacaaagct cggctgcctc tgcgggtctt cctgatcatt     420
ggcaacacca tggcgttcca gaatgacgtt tttgaatggt cccgagatca ccgtgcccac     480
cacaagtttt cagaaacgga tgccgacccc acaattccc gacgtggctt tttcttctct     540
cacgtgggtt ggctgcttgt gcgcaaacac ccagctgtca agaaaaaggg ttccacgcta     600
aatttatccg acctaagagc cgagaagctg gtgatgttcc agaggaggta ctacaaacct     660
ggtgtcctgt tgttgtgctt catcctgccc acactcgtgc crtggtatct gtgggatgaa     720
acgtttcaaa acagcctgtt ttttgccacc ttattccgtt aygcccttgg gctcaacgtc     780
acctggctgg tgaatagtgc tgcccatatg tatggatacc gcccttatga caagaccatc     840
```

```
aaccccgag agaatattct ggtttccctg ggagctgygg gtgagggctt ccacaactac      900
caccacacct ttccttatga ctactcagcc agtgagtacc gctggcacat caactttacc      960
acgttcttca ttgattgcat ggctgccatc ggtctggctt atgaccggaa gaaagtatcc     1020
aaggctgcca tcttggccag gataataaga actggagagg aaagctacaa gagtggctga     1080
atttgtggtc ccttgggttc cttttccaaa agccatctgg gcagaggttt aatgttctgt     1140
ttattaacta ctgaataatg ctaccaggat gctaaagatg acgttaaccc attacagtac     1200
agtattcttt aaaattttct ttttaaattg aaagccaaca actctgcctt tatgatgcta     1260
agctcatgtt cttatttctt ctcctatctt ctttctcttc tgttcccatt atccttccct     1320
ttgttttgtc cctgtcacct tcctttctcc ttctcctcat tgccccccag gcaagcaggt     1380
ggtcagtcat tggtgggttt ccagcttcca aagcctagac aaccctgctg tagtctcaaa     1440
ctagtgttct tgccccggc tgacccttc cttgagctgt ctgagcttta aggtggatgg     1500
ctcaagctag agatatgaca gaatcttctg ggaagggcct tgatgatctt cagcccagac     1560
ttttgctaaa tgaaatgaaa ataaacttta ttttggcacc aaactgaaaa acaggtcatt     1620
gtcaggggag aagtcagcat gcatggtgtg attgataaat aggatgagtt gaagtgggaa     1680
acaaggcagg aagctcctgc tgtgatcaga caccctgtc tgcccatcac ccagtatgct     1740
cccttctct cctgactctg ggaaatatct gtggagcagg gcagtcctaa aactcaaaag     1800
caaatctcaa tgtcctgata tactttaggc ttaggataaa gaagaagcat ttagtttgtg     1860
gtaaaagtgg tctctgctgc agacgaattg ttttctttct ttcayaacag gaagatttct     1920
tattctagat aacaagaaat cttgaggttg gttatttcca gaattgctga ttccagcagc     1980
tcaggaaatt gtcaaaattc tttcatcttt ctactctgcc atcttgggga tattggtcag     2040
ctcccctcat agtaagaaga tggctacagc attttgagac ttcaaaaaga gatacattgg     2100
tggtatggtg gtgagcatag ctgcctccca aaaaagaaag aattttagga gccagagttg     2160
ggtcaaacat aaagctatat atacatgggt actttggttg gaatattaaa gtaattctct     2220
tagagtattt ccctctgcaa aaaggaaggg gcttgcaaag aagaggaaga attagccagg     2280
ttccctcctt tccttctcgc tgctggacag gagatggaga ggttgagggg cagggtctgt     2340
aggcagttcc taagagatag ggttacaaaa gaaaggctct agatcacatt gctgggggat     2400
tcagaaggtt actaagtaag ttgttgggtg tcctgatata gaagctggtt atacaaacaa     2460
gttagatgtt gggttcattt cattaattcc actttctcct tggattgaga aagcattaga     2520
aggcttctcc ccacggtgtt gaacccttc actcattcct tctattacct tctagcggaa     2580
aatacaggac tggctggggg atggggtagg aatctctcaa ctaccctatc aattcttagg     2640
ctctgccatc tttgtccact ttctcctgct ggttttatct ccttgacgtt ccttcttt     2700
tctgacagg caagcctctt ctgtgtgtat tcagaggcag tgatggctac tgcagtccaa     2760
gttcgttccc tctcttactg acagaatggt cagggtcact gaaccactgt ttctctttac     2820
aaagttgagc aagctgccac tttcacttgg cctccagagt ctccatctat atccttgtgc     2880
tccttaccac actgatgact ccagacaagg ctggcaaagc ttgctagaaa catcctgggc     2940
acaggcattc gcactcatga ggcacggcca agccgaatgc atgttgtgcc agagccagcc     3000
atggagcaaa agagggattt gttttagtct tcctctgtct gggtcagaac cagagagcat     3060
gctggtgccc cgcttactgg ataagctgcc tacctgagtc agtgctccca gcggacagtg     3120
cgaggcttgc agaagcaggg ggygcctagc cttcactggg aagcacaaga agcaaaggca     3180
```

```
ggttccaaag tgcctcactc agaaggtggc cctagccccc tggagggagc cagggtgtac    3240
cgcaagacct tgactgaggc ttaggatgtg agatgccatg aactttgctg aacagtgtct    3300
ctgtttggca aactaaccag cattccccac aacacagtct agggcagacg rtagtataga    3360
ggagtgttgg aagaaccttg ggtcccttty tccctgtaac ctcagttgtc taggcagaaa    3420
cctggcttta ttctatttaa aggttgaaaa tatacaatac caaatgctct gccactgttg    3480
agctccaagg atggaaagga ggagaacatt tcttcctgta ttaattggat agatggrggc    3540
tacagagctt aggctaaact aaaggcatcg ttgtcttttg agttgttcct ctcagtagga    3600
aaaaaaaaaa tctaatggaa gatcactgta gattagatcc cctgaccaag cacctaccgc    3660
ttggaaatgc ctgtggggta gttttaatta cacaggtcat cagagttta attacacagg    3720 tcatcagatg catgcattac aaccgatgat caaaaccaac ttatctttct attctaattg    3780
tgttccgtgg atctgatcta taccatgacc ctacacaagg ctggatggtg tccttgggcc    3840
cagggtactt gtacttgtgt aggtgggggt tgtctactga gtaaggaata ctgtttttaa    3900
ggttctaaag ctaaattcaa atgatgcatt aatgacccaa aaactcagat ctgatggtgt    3960
ctgaatttct aacagtcctt gctttgtggg tatcctgaca acttatctgg atgccttaca    4020
tcttttctaa acagtgttgc ctctgaacgt gctctgctcc ctccctgctc cctctttgga    4080
gccccttggc accccagagc ctgcagaagt ggctggcata aaggggggcc tggctagaga    4140
atgatcagtg tagctgttg caggattcct ttctgggctt cattttggaa actttgctta    4200
gggctatttt tcttaattgc cacattgatg gaggtagaag gaattttgaa tgtatttgaa    4260
ttatatatta tttttttttt tttttagata aggatgggtg tagcattaaa atggaaattt    4320 tcccctggt tagctagtat cctgagtgta tcctctgtaa gtgtagctca aatgggtcat    4380
catgaaaagt tcaaaaaagc tcgatgtcaa agttatatgg gtggttaagg ccagggcctg    4440
tcctaccact gtgccactga cttgctatgt gaccctgggc aagtcattta actataatgt    4500
gcctcagtgt tccttctgtt aaaatgggat aataatactg acctacctca aagggcagtt    4560
ttgaggcatg actaatgctt tttataaagc atcttggaat tctctagttc tgagtattta    4620
tagtagcagt atccaccatg aagtgtgtcc accacgagcc acgtgtcctg gatgccgtca    4680
ggaatctata tggttctctc tgagagatgg aataaatgca tcagataaag ggtggrtaac    4740
tagccggaca aaatctggca atgcataaac tcattgccat ggaaacatac acacgatacc    4800
ttttccttaa ttgggtggga ttttccctt tttatgtggg atagtagtta tttgtgacct    4860
aagaataatt ttgaataat ttctattaat atcaactcca aagctagttg tactgatctg    4920
agattgtgtt tgttcataat aaaagtgaat ctgattgccc tgtg                     4964
```

<210> SEQ ID NO 2
<211> LENGTH: 359
<212> TYPE: PRT
<213> ORGANISM: Bos taurus

<400> SEQUENCE: 2

```
Met Pro Ala His Leu Leu Gln Glu Glu Ile Ser Ser Tyr Thr Thr
 1               5                  10                  15

Thr Thr Thr Ile Thr Ala Pro Pro Ser Arg Val Leu Gln Asn Gly Gly
                20                  25                  30

Gly Lys Leu Glu Lys Thr Pro Leu Tyr Leu Glu Glu Asp Ile Arg Pro
            35                  40                  45

Glu Met Arg Asp Asp Ile Tyr Asp Pro Thr Tyr Gln Asp Lys Glu Gly
        50                  55                  60
```

Pro Lys Pro Lys Leu Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
            85                  90                  95

Lys Ile Tyr Thr Tyr Ile Trp Val Leu Phe Tyr Tyr Leu Met Gly Ala
            100                 105                 110

Leu Gly Ile Thr Ala Gly Ala His Arg Leu Trp Ser His Arg Thr Tyr
            115                 120                 125

Lys Ala Arg Leu Pro Leu Arg Val Phe Leu Ile Ile Gly Asn Thr Met
130                 135                 140

Ala Phe Gln Asn Asp Val Phe Glu Trp Ser Arg Asp His Arg Ala His
145                 150                 155                 160

His Lys Phe Ser Glu Thr Asp Ala Asp Pro His Asn Ser Arg Arg Gly
            165                 170                 175

Phe Phe Phe Ser His Val Gly Trp Leu Leu Val Arg Lys His Pro Ala
            180                 185                 190

Val Lys Glu Lys Gly Ser Thr Leu Asn Leu Ser Asp Leu Arg Ala Glu
            195                 200                 205

Lys Leu Val Met Phe Gln Arg Arg Tyr Tyr Lys Pro Gly Val Leu Leu
210                 215                 220

Leu Cys Phe Ile Leu Pro Thr Leu Val Pro Trp Tyr Leu Trp Asp Glu
225                 230                 235                 240

Thr Phe Gln Asn Ser Leu Phe Phe Ala Thr Leu Phe Arg Tyr Ala Leu
            245                 250                 255

Gly Leu Asn Val Thr Trp Leu Val Asn Ser Ala Ala His Met Tyr Gly
            260                 265                 270

Tyr Arg Pro Tyr Asp Lys Thr Ile Asn Pro Arg Glu Asn Ile Leu Val
            275                 280                 285

Ser Leu Gly Ala Ala Gly Glu Gly Phe His Asn Tyr His His Thr Phe
            290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Ile Gly Leu Ala Tyr Asp Arg
                325                 330                 335

Lys Lys Val Ser Lys Ala Ala Ile Leu Ala Arg Ile Ile Arg Thr Gly
            340                 345                 350

Glu Glu Ser Tyr Lys Ser Gly
        355

<210> SEQ ID NO 3
<211> LENGTH: 24
<212> TYPE: DNA
<213> ORGANISM: Artificial
<220> FEATURE:
<223> OTHER INFORMATION: Designed oligonucleotide for DNA ampliciation
      by PCR

<400> SEQUENCE: 3
atgtatggat accgccctta tgac                                          24

<210> SEQ ID NO 4
<211> LENGTH: 26
<212> TYPE: DNA
<213> ORGANISM: Artificial
<220> FEATURE:
<223> OTHER INFORMATION: Designed oligonucleotide for DNA amplificiation
      by PCR

```
<400> SEQUENCE: 4
ctgtcccttg gttttatagt ggaatg                                   26

<210> SEQ ID NO 5
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 5
gtgtcctgtt gttgtgcttc atcctgcc                                 28

<210> SEQ ID NO 6
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 6
aatattctct cggggttga tggtcttg                                  28

<210> SEQ ID NO 7
<211> LENGTH: 24
<212> TYPE: DNA
<213> ORGANISM: Artificial
<220> FEATURE:
<223> OTHER INFORMATION: Designed oligonucleotide for DNA amplification
      by PCR

<400> SEQUENCE: 7
gttttttgcc accttattcc ggta                                     24

<210> SEQ ID NO 8
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 8
aatattctct cggggttga tggtcttg                                  28

<210> SEQ ID NO 9
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 9
gtgtcctgtt gttgtgcttc atcctgcc                                 28

<210> SEQ ID NO 10
<211> LENGTH: 27
<212> TYPE: DNA
<213> ORGANISM: Artificial
<220> FEATURE:
<223> OTHER INFORMATION: Designed oligonucleotide for DNA amplification
      by PCR
```

```
<400> SEQUENCE: 10
agccttggat actttcttcc ggtcata                                              27

<210> SEQ ID NO 11
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 11
aaaagcaggc tcaggaacta gtctacac                                             28

<210> SEQ ID NO 12
<211> LENGTH: 28
<212> TYPE: DNA
<213> ORGANISM: Artificial
<220> FEATURE:
<223> OTHER INFORMATION: Designed oligonucleotide for DNA amplification
      by PCR

<400> SEQUENCE: 12
ggggcaatga ggagaaggag aaaggaag                                             28

<210> SEQ ID NO 13
<211> LENGTH: 24
<212> TYPE: DNA
<213> ORGANISM: Artificial
<220> FEATURE:
<223> OTHER INFORMATION: Designed oligonucleotide for DNA amplification
      by PCR

<400> SEQUENCE: 13
gttttttgcc accttattcc ggta                                                 24

<210> SEQ ID NO 14
<211> LENGTH: 27
<212> TYPE: DNA
<213> ORGANISM: Artificial
<220> FEATURE:
<223> OTHER INFORMATION: Designed oligonucleotide for DNA amplification
      by PCR

<400> SEQUENCE: 14
agccttggat actttcttcc ggtcata                                              27
```

METHOD FOR EVALUATING QUALITY OF BEEF SUCH AS TASTE AND TEXTURE ON THE BASIS OF GENOTYPE OF STEAROYL-COA DESATURASE

TECHNICAL FIELD

The present invention relates to a method for evaluating the amount of the unsaturated fatty acid content in beef fat, based on the genotype of bovine stearoyl-CoA desaturase, and further relates to a method for predicting, based on its evaluation, quality of beef (beef taste and texture etc.). The present invention is useful for various fields such as animal science, beef industry (feeding, breeding, reproduction, etc.), processing of beef, dairy farming, and production and processing of dairy products (milk, and processed food such as butter, using milk for its raw material).

BACKGROUND ART

It is known that the content of unsaturated fatty acid in beef fat is associated with quality of beef, such as the beef taste and texture. Generally, if the content of unsaturated fatty acid is high with low melting point, the beef is considered to have good quality, which gives good taste and texture.

However, in order to judge whether the beef has such quality, there was no other way but to depend on the subjective (sensuous) method, in which the beef was actually eaten and evaluated. In other words, there was no conventional method, which was more objective, simple and efficient, like the judgment approach of predicting quality of beef, simply based on the genotype of a specific bovine gene.

By the way, stearoyl-CoA desaturase (SCD) is known as an enzyme which desaturates beef fat. This enzyme desaturates stearoyl-CoA which plays an important role for in vivo biosynthesis of lipids and their degradation. Amino acid sequence and cDNA sequence of bovine stearoyl-CoA (derived from Bos taurus) are shown in DDBJ/EMBL/GenBank databases; Accession number "AB075020". Information of these sequences was provided by inventors of the present invention.

As mentioned above, the content of unsaturated fatty acid in beef fat (in other words, the amount of the unsaturated fatty acid content) is associated with quality of beef, such as the beef taste and texture. If the amount of the unsaturated fatty acid content can be predicted on the basis of the genotype of a specific bovine gene, then it provides a new method which enables simple examination as to quality of beef, such as the beef taste and texture.

Such method based on the genotype is useful not only for evaluation and selection of cattle (beef cattle) with good quality of beef, but also for breeding and reproduction of cattle.

Furthermore, the content of unsaturated fatty acid in beef fat is associated with the cholesterol accumulation caused by beef intake, and it is considered one of important features of the cattle, especially in the countries where beef is eaten very often, such as the Europe and the United States of America. Therefore, the above-mentioned method for evaluating the unsaturated fatty acid content based on the genotype, is also useful from the view point of health care.

In addition, the content of unsaturated fatty acid in milk fat of the dairy cattle is considered to affect the taste and mouth-feel of dairy products, such as butter. For example, when the content of unsaturated fatty acid in milk fat is higher and the melting point is lower, then the butter produced by using the milk as raw material is softer with good mouth-melt. Therefore, the above-mentioned method for predicting the unsaturated fatty acid content based on the genotype, is also useful for dairy products and dairy cattle breeding.

DISCLOSURE OF THE INVENTION

The object of the present invention is (1) to provide a new method for simply and efficiently evaluating the amount of the unsaturated fatty acid content in beef fat on the basis of the genotype of a bovine gene, and (2) to provide a new method for predicting, based on its evaluation, quality of beef, such as the beef taste and texture, more objectively.

The inventors especially paid attention to the above-mentioned stearoyl-CoA desaturase gene, and studied about the relation between this gene and the unsaturated fatty acid percentage in beef fat, leading to the following findings that (1) eight single nucleotide polymorphisms (SNPs) were found out on this gene, (2) when classified according to the kind of the base at these SNPs, this gene can be roughly classified into two haplotypes, as the genotype of this gene, and (3) there were significant difference of unsaturated fatty acid content in beef fat between these two types. These findings led us to the present invention.

The present invention includes the following industrially useful inventions A) to I).

A) A method for predicting the amount of the unsaturated fatty acid content in beef fat (or milk fat), on the basis of a genotype of bovine stearoyl-CoA desaturase.

B) A method for predicting whether it is the cattle, from which good quality of beef (or dairy products) with good taste and texture can be produced, on the basis of the prediction in the method set forth in A) above.

C) The method set forth in A) or B), determining the genotype of bovine stearoyl-CoA desaturase by examination of at least one base among the following bases [1]-[8];

[1] the 702nd base in the base sequence of the gene shown in SEQ ID NO: 1 whose position corresponds to a single nucleotide polymorphism of either guanine (G) or adenine (A),

[2] the 762nd base in the base sequence of the gene shown in SEQ ID NO: 1 whose position corresponds to a single nucleotide polymorphism of either cytosine (C) or thymine (T),

[3] the 878th base in the base sequence of the gene shown in SEQ ID NO: 1 whose position corresponds to a single nucleotide polymorphism of either thymine (T) or cytosine (C),

[4] the 1905th base in the base sequence of the gene shown in SEQ ID NO: 1 whose position corresponds to a single nucleotide polymorphism of either thymine (T) or cytosine (C),

[5] the 3143rd base in the base sequence of the gene shown in SEQ ID NO: 1 whose position corresponds to a single nucleotide polymorphism of either cytosine (C) or thymine (T),

[6] the 3351st base in the base sequence of the gene shown in SEQ ID NO: 1 whose position corresponds to a single nucleotide polymorphism of either adenine (A) or guanine (G),

[7] the 3537th base in the base sequence of the gene shown in SEQ ID NO: 1 whose position corresponds to a single nucleotide polymorphism of either adenine (A) or guanine (G), and

[8] the 4736th base in the base sequence of the gene shown in SEQ ID NO: 1 whose position corresponds to a single nucleotide polymorphism of either adenine (A) or guanine (0).

D) The method set forth in C), comprising a step of amplifying a gene region including a base in any of the above bases [1]-[8], in which genomic DNA or cDNA prepared from a test cattle is used as a template, and a step of digesting thus amplified fragment with restriction enzyme, and judging the genotype of stearoyl-CoA desaturase by result of the digestion.

E) The method set forth in D), adopting the PCR (polymerase chain reaction) by use of a forward primer having a base sequence shown in SEQ ID NO: 5 and a reverse primer having a base sequence shown in SEQ ID NO: 6 in the amplification step, and using Nco I for the restriction enzyme in the digestion step.

F) The method set forth in C), examining at least one base among the above bases [1]-[8] by use of a gene polymorphism detector device such as a DNA chip.

G) A gene polymorphism detector device, used in the method set forth in C), comprising a probe for the examination of at least one base among the above bases [1]-[8].

H) The method set forth in any of A) to F), used for the judgment of quality of beef produced from a beef cattle such as Japanese Black cattle.

I) The method set forth in any of A) to F), used for the judgment of quality of milk produced from a dairy cattle such as the Holstein-Friesian cattle.

These and other objects, features and advantages of the present invention will become more apparent from the following description. Also, beneficial results of the present invention should be obvious from the following description when taken in conjunction with the accompanying drawings.

BRIEF DESCRIPTION OF THE DRAWINGS

FIG. 2 is a figure explaining primers etc., used in the judgment (PCR-RFLP method) of one embodiment of the present invention, nucleotides 1-1080 of SEQ ID NO: 1 are shown.

BEST MODE FOR CARRYING OUT THE INVENTION

Specific embodiments of the present invention are described in detail below with reference to the drawings.

(1) The Judgment Method of the Present Invention

The present invention is a method for predicting the amount of the unsaturated fatty acid content in beef fat or milk fat, based on the genotype of bovine stearoyl-CoA desaturase, as mentioned above.

Here, "cattle" means the animal belonging to Genus Bos, especially livestock cattle (Bos primigenius). The Europeane cattle (Bos taurus) and the Indian cattle (Bos indicus) are included in this "livestock cattle", and the following breeds of cattle are included in this "Europeane cattle (Bos taurus)"; i.e., Japanese cattle (such as Japanese Black, Japanese Brown, Japanese Polled and Japanese Shorthorn) and Europeane cattle (such as the Holstein-Friesian, the Jersey, the Shorthorn for meat, the Hereford and the Aberdeen Angus). The "cattle" used as a test animal (source of specimen) may be either the beef or the dairy cattle.

"Stearoyl-CoA desaturase" (hereafter, it is called "SCD" by its abbreviation) is an enzyme derived from cattle, which desaturates stearoyl-CoA. The cDNA sequence of bovine SCD gene is shown in SEQ ID NO: 1, which was isolated from Japanese Black and decided by the inventors, while the amino acid sequence of bovine SCD protein encoded by this gene is shown in SEQ ID NO: 2. These sequences of cDNA and amino acids are identical to those shown in DDBJ/EMBL/GenBank databases; Accession number "AB075020", except for the way of description at single nucleotide polymorphisms (SNPs).

Figure 1:
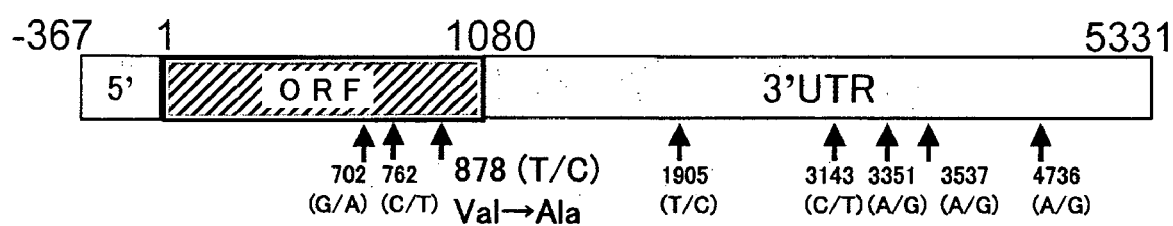
FIG. 1 is a figure explaining eight single nucleotide polymorphisms (SNPs) found out on bovine SCD gene.

FIG. 1 schematically shows the open reading frame (ORF) and the untranslated region (5'UTR and 3'UTR) of the above SCD gene. The first nucleotide of the ORF is set to the number "1", and each position is expressed by the number (=the number of nucleotides between each position and the first nucleotide of the ORF).

Eight of single nucleotide polymorphisms (SNPs) were found on the above SCD gene (including the untranslated region), as a result of investigation by the inventors. These eight SNPs are also shown in FIG. 1. These eight SNPs can be said mutations occurred on the SCD gene. Each position of these eight SNPs will be called a polymorphism position hereinafter, and the bases of these polymorphism positions will be called respectively [1] to [8] bases, numbered from the 5' side. These [1] to [8] bases are identified as follows;

[1] the 702nd base, which corresponds to a polymorphism position of either guanine (G) or adenine (A),
[2] the 762nd base, which corresponds to a polymorphism position of either cytosine (C) or thymine (T),
[3] the 878th base, which corresponds to a polymorphism position of either thymine (T) or cytosine (C),
[4] the 1905th base, which corresponds to a polymorphism position of either thymine (T) or cytosine (C),
[5] the 3143rd base, which corresponds to a polymorphism position of either cytosine (C) or thymine (T),
[6] the 3351st base, which corresponds to a polymorphism position of either adenine (A) or guanine (G),
[7] the 3537th base, which corresponds to a polymorphism position of either adenine (A) or guanine (G), and
[8] the 4736th base, which corresponds to a polymorphism position of either adenine (A) or guanine (G).

In the base sequence shown in SEQ ID NO: 1 each base of the above eight polymorphism positions is written by any of a universal cord "r" or "y".

Each base of the above eight polymorphism positions is identified by the number counted from the first nucleotide of the coding region (ORE) according to the cDNA sequence of the SCD gene shown in SEQ ID NO: 1, decided by the inventors. However, on the genomic DNA sequence of the SCD gene, each base of eight SNPs may be identified by a different number, when counted from the first nucleotide of start codon on the first exon, because of the existence of intron sequence. On the genomic DNA, therefore, the number of each base of eight SNPs should be interpreted in consideration of the existence of intron sequence (or, interpreted as the number on only the exons).

In addition, the cDNA sequence shown in SEQ ID NO: 1 is a sequence of the SCD gene isolated from Japanese Black, and there is a possibility that deletion and/or insertion of one or more bases have occurred on bovine SCD gene from any other breed of cattle than Japanese Black (especially, on the untranslated region (UTR)), by mutation etc. In such case, the number of each base of eight SNPs should be interpreted in consideration of the existence of the above deletion and/or insertion.

As shown in FIG. 1, three bases among the above-mentioned [1] to [8] bases, i.e., the [1] to [3] bases are located in the ORF. Moreover, it turned out that the [3] base, which corresponds to the 3rd polymorphism position, brings about replacement of the encoded amino acid, according to whether the [3] base is a thymine (T) or a cytosine (C). When the [3] base is a thymine (T), then the encoded amino acid is a valine (Val), whereas the encoded amino acid is an alanine (Ala) when the [3] base is a cytosine (C). Thus, replacement of the amino acid is brought about by change of the [3] base (in other words, the 878th base). The former genotype encoding the valine (Val) was called "V type" by the inventors, while the latter genotype encoding the alanine (Ala) was called "A type".

It was found that the above eight SNPs are not independent of each other, but linked to each other, as a result of investigation using a lot of gene samples. For example, when the 878th base was the thymine (T) which is a "V type", then all bases of other seven SNPs on the same gene were, in principle, bases written on the left-hand side of FIG. 1. On the contrary, when the 878th base was the cytosine (C) which is "A type", then all bases of other seven SNPs on the same gene were, in principle, bases written on the right-hand side of FIG. 1. Accordingly, indirect examination of the 878th base is available by the examination of any base of other seven SNPs, in order to decide whether the genotype is "V type" or "A type", instead of direct examination of the 878th base.

Exceptionally, in rare cases, there were genes on which the 878th base was not linked to other seven SNPs in the above-mentioned manner. However, even in such cases, the three bases on the ORF, i.e., the [1] to [3] bases were linked to each other in the above-mentioned manner. Therefore, even in such cases, indirect examination of the 878th base is available by the examination of the 702nd base or the 762nd base, in order to decide whether the genotype is "V type" or "A type".

Thus, it was found that the genotype of bovine SCD gene can be roughly classified into two haplotypes of "V type" and "A type". Further investigation revealed that the genotype of bovine SCD gene is associated with fatty acid composition (in other words, "the content of unsaturated fatty acid in beef fat" or "the amount of the unsaturated fatty acid content"). That is, it was found that there is significant difference between the above "V type" and "A type" in the content of unsaturated fatty acid in beef fat. Although details of the investigation will be explained in the Example as described later (for instance, see Table 1), the percentage of mono-unsaturated fatty acid (MUFA) content in beef fat was the highest when the genotype of bovine SCD gene was (A/A) having homozygous A type. When the genotype of bovine SCD gene was (V/A) having heterozygous of V and A type, the percentage was higher than that in the case of the genotype (V/V) having homozygous V type.

As mentioned above, the content of unsaturated fatty acid in beef fat is associated with quality of beef such as taste (flavor) and texture. In general, if the content of unsaturated fatty acid is high and melting point of beef fat is low, the beef is considered to have good quality, which gives good taste and texture. Therefore, if the genotype of bovine SCD gene is (A/A), such cattle with (A/A) can be evaluated (estimated) to produce better quality of beef (better taste and texture), compared with the cattle with (V/V). Thus, by examining the genotype of bovine SCD gene, it becomes possible not only to judge the content of unsaturated fatty acid in beef fat, but also to judge whether it is the cattle, from which high quality of beef (with better taste and texture) can be produced.

Furthermore, we investigated about the Holstein-Friesian in the same manner, and similar results were obtained that the genotype of bovine SCD gene was associated with the unsaturated fatty acid content in beef fat, and that the content was higher in "A type" than in "V type". Taking it into consideration that the females of the Holstein-Friesian are dairy cattle, it is considered that the content of unsaturated fatty acid in milk fat could be also higher in "A type" than in "V type". As for milk used for the raw material of dairy products such as butter, if the content of unsaturated fatty acid in milk fat is high and the melting point of the milk is low, the dairy products could be softer. Thus, by examining the genotype of bovine SCD gene, it could be possible to predict the content of unsaturated fatty acid in milk fat, and further to predict whether it is the cattle, from which better quality of dairy products (milk, and processed food such as butter with softer taste and better mouthfeel) can be produced.

In the method of the present invention, the method for examining the genotype of bovine SCD gene should be not limited, and various known methods can be applied to the method for directly, or indirectly, examining whether the 878th base on bovine SCD gene is thymine (T) or cytosine (C). The PCR-RFLP method is an easy and simple method with good accuracy, to examine any base of the above [1] to [3] bases, and to decide the genotype of bovine SCD gene. The following is a brief explanation of the judgment using this PCR-RFLP method.

(2) Method for Judging the SCD Genotype by the PCR-RFLP Method

Genetic sample (specimen) for the judgment is may be either genomic DNA or cDNA. The genomic DNA can be extracted and purified by a known method from any organ, tissue or cell of the test cattle (origin of specimen). Extraction of the organ, tissue or cell from the test cattle may be carried out before slaughter, or after slaughter. The cell from the test cattle may be blood (the cell in blood), the cell in the amniotic fluid, or the cultured cell (obtained from extracted tissue etc.). The genomic DNA was prepared from the muscular tissue in the Example as described later. The cDNA can be synthesized from mRNA by a known method with the reverse transcriptase. The mRNA can be extracted and purified by a known method from any organ, tissue or cell of the test cattle.

The genomic DNA or cDNA prepared by the above method is used as a template in the PCR (Polymerase Chain Reaction) method, for the purpose of determination of the base at SNP position (i.e., SNP typing). After amplifying a target region within SCD gene (including one base among the above [1] to [3] bases) by such PCR method, the amplified fragment is digested with a suitable restriction enzyme. The genotype of bovine SCD gene can be judged (determined) according to the result as to whether the fragment was digested or not.

The above PCR method should be not limited about each condition of the method, used reagents, primers and restriction enzyme, etc. The following are explanations about the methods, which were adopted in the Example as described later. The explanations are divided into two cases; one case where genomic DNA was used as a genetic sample (specimen), and the other case where cDNA was used as a genetic sample.

[A] The Case where Genomic DNA was Used as a Genetic Sample

The composition of the PCR solution was as follows; genomic DNA 20 ng, TaKaRa Ex Taq polymerase HS 0.5 Unit, 10× Taq polymerase buffer 2.0 µl, 25 mM dNTP mix 1.6 µl, each 1.0 µl of forward primer (10 pmol) and reverse primer (10 pmol), and ultrapure water added to be total 20 μl of solution. Primers and restriction enzyme used in the PCR were different according to which base was examined among the above [1] to [3] bases, as follows.

[A-1] The Case where the 878th Base was Directly Examined

In this case, designed sequences of forward primer and reverse primer are shown in the following (a) and (b) respectively.

(a) 5'-ATgTATggATACCgCCCTTATgAC-3'    (SEQ ID NO: 3)

(b) 5'-CTgTCCCTTAgTTTTATAgTggAATg-3'   (SEQ ID NO: 4)

The sequence of the reverse primer was designed based on a specific base sequence within intron. The PCR was carried out by the following condition; firstly (1) 94° C. for 2 minutes, next (2) 35 cycles of 94° C. for 30 seconds/65° C. for 30 seconds/72° C. for 1 minute, followed by (3) 72° C. for 7 minutes.

The amplified fragment (PCR product) obtained by the above PCR was 323 bp. This PCR product was subjected to digestion by the restriction enzyme Fnu 4HI. If the base on this PCR product, corresponding to the 878th base, is the thymine, then the PCR product will be not cut (digested) at this position by the above restriction enzyme. In this case (where the PCR product was not cut), the genotype of a test cattle (specimen) is judged the V type, because the valine is coded in this case by the codon including the 878th base. On the other hand, if the base on this PCR product, corresponding to the 878th base, is the cytosine, then the PCR product will be cut (digested) at this position by the above restriction enzyme Fnu 4HI. In this case (where the PCR product was cut), the genotype of a test cattle (specimen) is judged the A type.

[A-2] The Case where the 702nd Base was Examined

In this case, designed sequences of forward primer and reverse primer are shown in the following (c) and (d) respectively.

(c) 5'-gTgTCCTgTTgTTgTgCTTCATCCTgCC-3'   (SEQ ID NO: 5)

(d) 5'-AATATTCTCTCggggTTgATggTCTTg-3'   (SEQ ID NO: 6)

The PCR condition was the same as the condition described in the above [A-1]. The amplified fragment (PCR product) obtained by this PCR was 392 bp. This PCR product was subjected to digestion by the restriction enzyme Nco I. If the base on this PCR product, corresponding to the 702nd base, is the adenine, then the PCR product will be cut (digested) at this position by the above restriction enzyme. In this case (where the PCR product was cut), the genotype of a test cattle (specimen) is judged the A type, because the 878th base is the cytosine in this case. On the other hand, if the base on this PCR product, corresponding to the 702nd base, is the guanine, then the PCR product will be not cut (digested) at this position by the above restriction enzyme Nco I. In this case (where the PCR product was not cut), the genotype of a test cattle (specimen) is judged the V type.

[A-3] The Case where the 762nd Base was Examined

In this case, designed sequences of forward primer and reverse primer are shown in the following (e) and (f) respectively.

(e) 5'-gTTTTTTgCCACCTTATTCCg(g)TA-3'   (SEQ ID NO: 7)

(f) 5'-AATATTCTCTCggggGTTgATggTCTTg-3'   (SEQ ID NO: 8)

The 22nd base was designed to be a guanine (g) in the above forward primer, although its base is a thymine on the corresponding sequence of bovine SCD gene. This was to make the recognition site of the restriction enzyme Rsa I on the PCR product.

The PCR condition was the same as the condition described in the above [A-1], except that the temperature 65° C. in the step (2) was changed to 60° C. The PCR product obtained by this PCR was 121 bp. This PCR product was subjected to digestion by the restriction enzyme Rsa I. If the base on this PCR product, corresponding to the 762nd base, is the cytosine, then the PCR product will be cut at this position by the above restriction enzyme. In this case (where the PCR product was cut), the genotype of a test cattle is judged the V type, because the 878th base is the thymine in this case. On the other hand, if the base on this PCR product, corresponding to the 762nd base, is the thymine, then the PCR product will be not cut at this position by the above restriction enzyme Rsa I. In this case (where the PCR product was not cut), the genotype of a test cattle is judged the A type.

[B] The Case where cDNA was Used as a Genetic Sample

The composition of the PCR solution was as follows; cDNA 20 ng, TaKaRa Ex Taq polymerase HS 0.5 Unit, 10×Taq polymerase buffer 2.0 μl, 25 mM dNTP mix 1.6 μl, each 1.0 μl of forward primer (10 pmol) and reverse primer (10 pmol), and ultrapure water added to be total 20 μl of solution. Primers and restriction enzyme used in the PCR were different according to which base was examined among the above [1] to [3] bases, as follows.

[B-1] The Case where the 878th Base was Directly Examined

In this case, designed sequences of forward primer and reverse primer are shown in the following (g) and (h) respectively.

(g) 5'-gTgTCCTgTTgTTgTgCTTCATCCTgCC-3'   (SEQ ID NO: 9)

(h) 5'-AgCCTTggATACTTTCTTCCggTCATA-3'   (SEQ ID NO: 10)

The PCR condition was the same as the condition described in the above [A-1]. The PCR product obtained by this PCR was 335 bp. This PCR product was subjected to digestion by the restriction enzyme Fnu 4HI. If the base on this PCR product, corresponding to the 878th base, is the thymine, then the PCR product will be not cut at this position by the above restriction enzyme. In this case (where the PCR product was not cut), the genotype of a test cattle is judged the V type, because the valine is coded in this case by the codon including the 878th base. On the other hand, if the base on this PCR product, corresponding to the 878th base, is the cytosine, then the PCR product will be cut at this position by the above restriction enzyme Fnu 4HI. In this case (where the PCR product was cut), the genotype of a test cattle is judged the A type.

[B-2] The Case where the 702nd Base was Examined

In this case, designed sequences of forward primer and reverse primer are shown in the following (i) and (j) respectively.

```
(i) 5'-AAAAgCAggCTCAggAACTAgTCTACAC-3'    (SEQ ID NO: 11)

(j) 5'-ggggCAATgAggAgAAggAgAAAggAAg-3'    (SEQ ID NO: 12)
```

The PCR condition was the same as the condition described in the above [A-1]. The PCR product obtained by this PCR was 1468 bp. This PCR product was subjected to digestion by the restriction enzyme Nco I. If the base on this PCR product, corresponding to the 702nd base, is the adenine, then the PCR product will be cut at this position by the above restriction enzyme. In this case (where the PCR product was cut), the genotype of a test cattle is judged the A type, because the 878th base is the cytosine in this case. On the other hand, if the base on this PCR product, corresponding to the 702nd base, is the guanine, then the PCR product will be not cut at this position by the above restriction enzyme Nco I. In this case (where the PCR product was not cut), the genotype of a test cattle is judged the V type.

[B-3] The Case where the 762nd Base was Examined

In this case, designed sequences of forward primer and reverse primer are shown in the following (k) and (l) respectively.

```
(k) 5'-gTTTTTTgCCACCTTATTCCg(g)TA-3'    (SEQ ID NO: 13)

(l) 5'-AgCCTTggATACTTTCTTCCggTCATA-3'   (SEQ ID NO: 14)
```

The 22nd base was designed to be a guanine (g) in the above forward primer, although its base is a thymine on the corresponding sequence of bovine SCD gene. This was to make the recognition site of the restriction enzyme Rsa I on the PCR product.

The PCR condition was the same as the condition described in the above [A-3]. The PCR product obtained by this PCR was 265 bp. This PCR product was subjected to digestion by the restriction enzyme Rsa I. If the base on this PCR product, corresponding to the 762nd base, is the cytosine, then the PCR product will be cut at this position by the above restriction enzyme. In this case (where the PCR product was cut), the genotype of a test cattle is judged the V type, because the 878th base is the thymine in this case. On the other hand, if the base on this PCR product, corresponding to the 762nd base, is the thymine, then the PCR product will be not cut at this position by the above restriction enzyme Rsa I. In this case (where the PCR product was not cut), the genotype of a test cattle is judged the A type.

In all of the above-mentioned PCR-RFLP methods, the digestion by each restriction enzymes was carried out as follows; firstly, the reaction solution was prepared, whose composition was PCR product 10 µl, restriction enzyme 2 Unit, buffer for each restriction enzyme 2.0 µl, and ultrapure water added to be total 20 µl of solution. Then, the reaction solution was subjected to incubation at 37° C. overnight, followed by the electrophoresis which was carried out at 100V for 30 minutes with 3.0% agarose gel.

Figure 3:
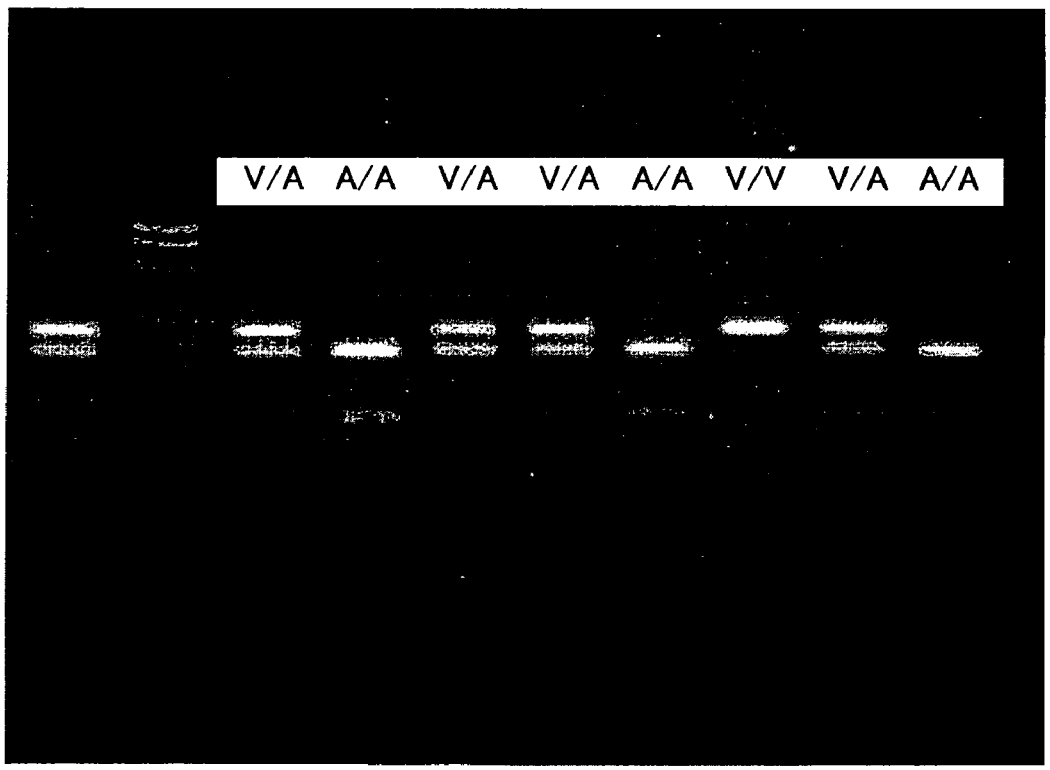
FIG. 3 shows the result of electrophoresis in the judgment of one embodiment of the present invention.

FIG. 3 shows a result of the electrophoresis. This result was in the case of the above [A-2] (i.e., the case where genomic DNA was used as a genetic sample, and the 702nd base was examined). The method of this case was used in the below-mentioned Example, in order to judge the genotype of bovine SCD gene. As shown in FIG. 3, when only shorter DNA band appeared, then the genotype of a test cattle is judged the type (A/A). When only longer DNA band appeared, then the genotype is judged the type (V/V). When both of shorter and longer DNA bands appeared, then the genotype is judged the type (V/A). Thus, this PCR-RFLP method enables simple and precise judgment of the genotype of bovine SCD gene.

(3) Other Embodiments of the Present Invention

The method of the present invention is not limited to the PCR-RFLP method described in the above (2). For example, each condition for reaction, used reagents, primers or restriction enzymes, etc. can be variously changed, even when using the PCR-RFLP method. It is, however, remarkable that each primer set was designed in the above-mentioned PCR-RFLP method, so as to include another restriction site of used restriction enzyme on the fragment amplified by the PCR, in addition to the restriction site at each polymorphism position. This was to confirm heterozygote detection and to eliminate the possibility of failure of cutting by each restriction enzyme. Moreover, in order to avoid overlapping of different DNA bands on the electrophoresis, each primer position was determined so that DNA fragments made by digestion might be different in their length from each other.

Of course, in addition to the PCR-RFLP method, other methods may be used for the judgment (method) of the present invention. If it is a method which enables direct and indirect examination of the above [3] base (the 878th base) on bovine SCD gene, its method is available as the method of the present invention. Such method includes various known methods; for example, the method of detecting point mutation on a base sequence, and the method of detecting a base at SNP position (SNP typing) (for reference, see "Genome science of post-sequence; (1) Strategy of SNP gene polymorphism" (Nakayama Shoten)).

One example of the above SNP typing is a method by use of gene polymorphism detector tool (device) such as a DNA chip. This SNP typing method is characterized by detection of hybridization signal between a probe and a genetic sample prepared from a test animal, using the DNA chip (or, similar device) that comprises, on a substrate, the probe to detect at least one base among the above [1] to [8] bases. The probe can be designed based on a base sequence including at least one of the above eight SNPs, or its complementary sequence. Here, the word "DNA chip" principally means a synthesized-type DNA chip, comprising a synthesized oligonucleotide as the probe, but also includes an attached-type DNA microarray, comprising attached cDNA such as PCR product as the probe. The gene polymorphism detector tool, such as the DNA chip, is available to the method of the present invention, and also included in the present invention.

Other methods of the present invention include a method for detecting point mutation, such as PCR-SSCP method, and an amplification method other than the PCR, such as RCA method. Instead of the RFLP (Restriction Fragment Length Polymorphism) method, SNP typing is also possible by direct sequencing of amplified fragment using a sequencer, after DNA amplification.

In addition to the above eight SNPs, other mutation may have happened on the base sequence of bovine SCD gene, among animals belonging to Genus Bos (even among animals belonging to the European cattle (Bos taurus)). That is, there is a possibility of existence of the cattle, whose cDNA sequence is different, in a strict sense, from the sequence shown in SEQ ID NO: 1. However, even if so, the prediction of the content of unsaturated fatty acid in beef (or milk) fat is also possible to such cattle, by investigating the genotype of bovine SCD gene using the above-mentioned method of the present invention.

Moreover, there is a possibility that artificial mutation has been introduced on the SCD gene when the test cattle is artificially produced by recombinant DNA technology etc. However, even if so, the method of the present invention is also available to such cattle, in the above-mentioned manner.

Genetic sample prepared from a test cattle may be either DNA or RNA. The method for preparation should be not limited. The genotype of bovine SCD gene can be determined based on the sequence of intron or untranslated region (UTR), as well as coding sequence which is encoding protein.

(4) Industrial Applicability (Utility) of the Present Invention

The present invention is a method of predicting fatty acid composition (the unsaturated fatty acid percentage in fat), on the basis of the genotype of bovine SCD gene. The present invention is useful for various fields such as animal science, livestock industry (feeding, breeding, reproduction, etc.), beef industry, dairy farming, and dairy production.

As mentioned above, the content of unsaturated fatty acid in beef fat is associated with quality of beef, such as taste and texture. Generally, if the unsaturated fatty acid percentage is high and the beef melting point is low, the beef is considered to have good quality, which gives good taste and texture. Accordingly, the present invention can be used for evaluation of beef quality from the beef cattle such as Japanese Black cattle. Moreover, the present invention can be used, through the above evaluation, for breeding and reproduction. That is, the present invention may be applied to the breeding strategy to produce a superiol herd which has the characteristics of high quality beef producer.

Additionally, when the content of unsaturated fatty acid in milk fat is higher and the melting point is lower, then the dairy products (such as butter) would be softer with good mouth-melt by use of such milk for the raw material. Therefore, the present invention may be used for evaluation of quality of milk produced from the dairy cattle such as the Holstein-Friesian. Also, the present invention may be used, through the above evaluation, for dairy cattle breeding and reproduction.

The unsaturated fatty acid content in beef fat is associated with the cholesterol accumulation caused by beef intake. The present invention enables prediction of the unsaturated fatty acid content and therefore, it is also useful from the view point of human health. For example, development of the beef with lower melting point is important for production and development of a healthy beef (good beef for health), especially in the countries where beef is eaten very often, such as the Europe and the United States of America.

The present invention is available to various fields such as animal science and livestock industry, through selection and reproduction of a target cattle or reproduction by using sperm or fertilized egg, etc. For example, the present invention is available to reproduction using recombinant DNA technology etc., as well as various gene experiments. Also, the present invention is applicable to prenatal diagnosis Judgment) for reproduction. Such prenatal diagnosis includes the method to pick up embryo cell from the amniotic fluid of the uterus, to prepare genetic samples and to prepare selected eggs which will produce high quality beef.

The present invention is described in detail below through Example thereof, but in no way is the present invention limited to this Example.

In this Example, evaluation was carried out by the above-mentioned PCR-RFLP method in which the genomic DNA was prepared from Japanese Black and used as the genetic sample (specimen). The genotype of bovine SCD gene was judged whether it was the V type or the A type, through examination of the 702nd base. Used reagents and condition for reaction, etc. are described above, and here omitted explanation thereof. FIG. 2 shows base sequence of the translated region (ORF) of SCD cDNA, and also shows each position, to which forward primer and reverse primer were designed and used for the PCR method. The sequence of CCATGG, enclosed with square in FIG. 2 shows the restriction site of Nco I. The third base among this sequence corresponds to the 702nd base at SNP. When this base is "A" (adenine), shorter DNA fragment is produced because PCR product is cut with Nco I. In this case (shorter DNA fragment is produced), its genotype is judged the A type because the 878th base is "C" (cytosine). On the other hand, when the 702nd base is "G" (guanine), shorter DNA fragment is not produced because PCR product is not cut with Nco I. In this case (shorter DNA fragment is not produced), its genotype is judged the V type because the 878th base is "T" (thymine) (FIG. 3).

The following Table 1 is the result of determining the genotype of each test cattle by the above method. Table 1 also shows, in its right column, the result of measurement of the unsaturated fatty acid content in the kidney knob fat, for each genotype.

TABLE 1

|  | Number | Mean ± S.E. |
| --- | --- | --- |
| A/A | 69 | 52.5 ± 0.5$^a$ |
| V/A | 36 | 50.9 ± 0.6$^b$ |
| V/V | 42 | 48.6 ± 0.7$^c$ |

As shown in Table 1, the unsaturated fatty acid percentage was the highest in the genotype (A/A) and it was higher in the genotype (V/A) than the genotype (V/V), which is a result of analysis of variance in one factor of SCD genotype. Little letters "a", "b" and "c" in Table 1 show the significant difference by the risk 5% or less.

Similarly, we investigated the difference of the content of unsaturated fatty acid in the fat from the rib-eye area, among these SCD genotypes. The result is shown in the following Table 2.

TABLE 2

|  | Number | Mean ± S.E. |
| --- | --- | --- |
| A/A | 48 | 56.3 ± 0.6 |
| V/A | 23 | 56.3 ± 0.5 |
| V/V | 5 | 53.5 ± 0.7 |

In this case, significant difference in the unsaturated fatty acid percentage was not obtained among these SCD genotypes. However, as shown in Table 2, the unsaturated fatty acid percentage was higher in the genotype (A/A) than the genotype (V/V), when these genotypes were compared.

Moreover, we investigated the difference of the content of unsaturated fatty acid in the fat from the trapezius muscle, among these SCD genotypes. The result is shown in the following Table 3.

TABLE 3

|  | Frequency of the Genotype (%) | Number | MUFA content (%) Mean ± S.E. | Melting Point (° C.) Mean ± S.E. |
| --- | --- | --- | --- | --- |
| A/A | 18.5 | 74 | 59.4 ± 0.2$^a$ | 24.9 ± 0.4$^a$ |
| V/A | 73.7 | 295 | 58.3 ± 0.1$^b$ | 26.3 ± 0.2$^b$ |
| V/V | 7.8 | 31 | 57.0 ± 0.4$^c$ | 27.5 ± 0.5$^c$ |

As shown in Table 3, the unsaturated fatty acid percentage was the highest in the genotype (A/A) and it was higher in the genotype (V/A) than the genotype (V/V), which is a result of analysis of variance in one factor of SCD genotype. Little letters "a", "b" and "c" in Table 3 show the significant difference. "MUFA" is a total of mono-unsaturated fatty acids.

Table 3 also shows the comparison of melting point. This result supports that, when the unsaturated fatty acid percentage is higher, the beef melting point is lower and the beef may have better quality, which gives better taste and texture.

Next, we investigated the difference in frequency of these SCD genotypes among various regions. The result is shown in the following Table 4.

TABLE 4

| Region | Number | Frequency of the Genotype (%) | | | Frequency of the Genotype | |
| --- | --- | --- | --- | --- | --- | --- |
| | | A/A | V/A | V/V | A | V |
| Y G | 38 | 36.8 | 60.5 | 2.6 | 0.67 | 0.33 |
| T T | 38 | 44.7 | 50.0 | 5.3 | 0.70 | 0.30 |
| B G | 36 | 25.0 | 52.8 | 22.2 | 0.51 | 0.49 |
| S S | 39 | 30.8 | 46.1 | 23.1 | 0.54 | 0.46 |
| S M | 40 | 0.0 | 37.5 | 62.5 | 0.19 | 0.81 |
| K M | 17 | 35.5 | 58.8 | 5.9 | 0.65 | 0.35 |
| K G | 45 | 55.6 | 44.4 | 0.0 | 0.78 | 0.22 |

All of the investigated cattle were the beef cattle shipped from various regions to the Osaka market from July to September in 2002. In Table 4, each region is shown by the symbol of two letters. As shown in Table 4, frequency of each SCD genotype was different according to the regions. In this investigation, the frequency of the A type was high in the Tajima strain (cattle in the Tajima region) evaluated as high quality beef.

We also investigated the SCD genotype of the Holstein-Friesian and the relation between the SCD genotype and the unsaturated fatty acid percentage in fat. The result was that the unsaturated fatty acid percentage was higher in the A type than in the V type, similarly to the result of Japanese Black. This result shows that the SCD genotype is associated with the unsaturated fatty acid percentage in fat, not only in Japanese Black but also in other cattle breeds.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

INDUSTRIAL APPLICABILITY

As mentioned above, the present invention is a method of predicting the unsaturated fatty acid percentage in beef (or milk) fat, on the basis of the genotype of bovine SCD gene, and useful for various fields such as animal science and livestock industry, including evaluation as to whether it is a cattle from which good quality of beef (or dairy products) can be produced in breeding and reproduction.

The invention claimed is:

1. A method for identifying a bovine animal likely to have a higher percentage of monounsaturated fatty acid (MUFA) content in beef fat obtained from said bovine animal, said method comprising:

obtaining a biological sample from said bovine animal, said sample comprising nucleic acids from said bovine animal; and detecting in said nucleic acids the presence of an A allele of a bovine stearoyl-CoA desaturase (SCD) gene, wherein determining the presence of said A allele comprises detecting: (i) an A nucleotide in the bovine SCD gene at a position corresponding to position 702 of SEQ ID NO: 1; (ii) a T nucleotide in the bovine SCD gene at a position corresponding to position 762 of SEQ ID NO: 1; or (iii) a C nucleotide in the bovine SCD gene at a position corresponding to position 878 of SEQ ID NO: 1; and correlating the presence of the A allele with a higher percentage of MUFA content in beef fat obtained from said bovine animal.

2. A method for identifying a bovine animal according to claim 1, wherein the presence of the A allele is associated with a higher percentage of MUFA in beef fat and a higher percentage of MUFA in beef fat effects beef taste and texture.

3. The method according to claim 1, comprising preparing genomic DNA or cDNA from a test cattle, amplifying a gene region including any of the nucleotides set forth in (i)-(iii), and digesting thus amplified fragment with a restriction enzyme, and determining the A allele as a result of the digestion.

4. The method according to claim 3, comprising a PCR reaction with SEQ ID NO: 5 and SEQ ID NO: 6 in the amplification step, and NcoI as the restriction enzyme in the digestion step.

5. The method according to claim 1, comprising examining at least one nucleotide as set forth in (i)-(iii) with a gene polymorphism detector device such as a DNA chip.

6. The method according to claim 1 used to evaluate an amount of MUFA produced from beef cattle including a Japanese Black cattle.

* * * * *